United States Patent [19]

Ellerbe

[11] Patent Number: 4,749,656
[45] Date of Patent: Jun. 7, 1988

[54] ANALYTICAL METHOD FOR DETERMINING ESSENTIAL COMPONENTS OF A STRETFORD GAS TREATING PROCESS SOLUTION

[75] Inventor: LaVerne W. Ellerbe, Southington, Conn.

[73] Assignee: The Dow Chemical Company, Midland, Mich.

[21] Appl. No.: 900,011

[22] Filed: Aug. 25, 1986

Related U.S. Application Data

[63] Continuation-in-part of Ser. No. 718,044, Mar. 29, 1985, abandoned.

[51] Int. Cl.$^4$ ............... B01J 1/04; C02F 1/42; G01N 30/02; G01N 30/96
[52] U.S. Cl. ...................... 436/83; 436/100; 436/119; 436/127; 436/133; 436/161; 73/61.1 C; 210/662
[58] Field of Search ............... 436/83, 100-102, 436/119, 128, 133, 179, 161, 127; 422/70; 210/370, 374, 638, 66 D, 661-662, 670, 683, 684; 423/62, 63, 226, 514, 521, 573 R; 73/61.1 C, 61.1 R; 260/370

[56] References Cited

U.S. PATENT DOCUMENTS

| | | | |
|---|---|---|---|
| 3,961,034 | 6/1976 | Bostian et al. | 423/514 X |
| 4,252,537 | 2/1981 | Cattran et al. | 436/161 X |
| 4,260,590 | 4/1981 | Weber | 423/226 |
| 4,385,044 | 5/1983 | Wolcott | 423/226 |
| 4,518,504 | 5/1985 | Wolcott | 210/674 X |
| 4,537,752 | 8/1985 | Weber | 423/226 X |
| 4,581,128 | 4/1986 | Plummer et al. | 423/573 R |

FOREIGN PATENT DOCUMENTS

| | | | |
|---|---|---|---|
| 3005163 | 8/1981 | Fed. Rep. of Germany | 423/63 |
| 8082161 | 5/1983 | Japan | 423/161 |

*Primary Examiner*—David L. Lacey
*Assistant Examiner*—Jill Johnston

[57] ABSTRACT

A method for determining the presence of an amount of sodium vanadate, in an aqueous solution containing the same which may also contain one or more sodium acid carbonate, sodium carbonate, sodium thiosulfate, anthraquinone disulfonic acid, sodium sulfate, various acid gases (e.g. $H_2S$, $CO_2$, COS and the like) and hydrocarbon liquid and gases such as would be expected in a Stretford gas treating solution, the improvement which comprises passing the solution to be analyzed into and through an anion exchange guard column then through a brine sensitive medium capacity ( 0.05 meq./gm) hydrophobic anion exchange column eluting the columns with a 0.001 M $Na_2SO_4$/0.0004 M NaOH aqueous eluant solution and detecting the sodium vanadate and sodium carbonate, sodium bicarbonate, sodium hydroxide and sodium thiosulfate, if present in a zinc source ultra violet detector and anthraquinone in a mercury source ultra violet 254 nm detector, or deuterium source 190 nm detector recording the signal(s) from the detector thereby obtaining relative proportionation of the aforesaid detected compounds in the solution.

4 Claims, 2 Drawing Sheets

ANALYTICAL METHOD FOR DETERMINING ESSENTIAL COMPONENTS OF A STRETFORD GAS TREATING PROCESS SOLUTION

CROSS REFERENCE TO THE RELATED APPLICATION

This application is a continuation-in-part of application Ser. No. 718,044 filed Mar. 29, 1985, now abandoned.

BACKGROUND OF THE INVENTION

Analysis for elements and compounds within industrial solutions is essential to proper and economic utilization of most commercial scale processes. For the most part modification of laboratory analytical equipment simplified for use to analyze a component or components in a particular process stream has been adequate. However, some elements and compounds of these elements are not widely employed in the industrial world and many of these elements are still analyzed by the older time consuming analytical techniques. For example, vanadium is still analyzed by the wet ash method. When an element or its compound, such as sodium vanadate, is found in admixture with other compounds, as for example, a Stretford process solution for removing acid gases from natural and synthetic gases, the analysis may require several analytical procedures and is so time consuming that partial adjustment of the various components in the treating solution is more or less haphazard resulting in large swings in treating gas acid gas content. Thus, during operation of an acid gas treating process, for example, that known as the "Stretford Process", it is necessary to determine the concentration of several of the essential components of the absorbent liquid to enable replenishment of these components from time to time to maintain an economic process whose products meet a specific acid gas specification, four aliquots of the solution have to be analyzed, each aliquot treated in a different manner. The total analysis takes about one and a half hours. The separate analyses are: sodium hydroxide titration which takes about 5 minutes, total carbonate alkalinity titration which takes about one hour, sodium vanadate by the wet-ash method including the blank which takes about one hour and sodium thiosulfate and its blank which takes about 15 minutes. These analytical methods usually are accurate to about ±5% in the presence of the Stretford matrix.

It would therefore be advantageous to have available an analytical method which would give results for all four components in about 20 minutes using a single sample or aliquot. Similarly it would be advantageous to have available a method which can be used in a complex matrix such as the Stretford streams but also can be used where one or more of these components is present.

BRIEF DESCRIPTION OF THE INVENTION

In accordance with the present invention there is disclosed a simple ion exchange technique coupled with specific U.V. detectors whereby the analysis for total carbonate alkalinity ($Na_2CO_3$/$NaHCO_3$), vanadium as sodium vanadate, sodium thiosulfate and sodium hydroxide as found in a Stretford acid gas removal process solution as well as these elements/compounds in other solutions can be made in about twenty minutes. The key to this analytical technique is of course the selection of the column and the detector. In the instant case the column is of medium capacity (0.05 meq./gm) anion exchange resin treated for analysis of hydrophobic ions and a similar column treated for analysis of brine. The only known commercially available resin is that produced by Dionex Corp. and sold under the tradename Dionex AG.5 or AS.5—separator.

The detector employs metal sources which give absorbance at 214 n.m. wave length, such as zinc.

Also in the Stretford process solution, the presence of anthraquinone may be determined in the same column by using a 190 n.m. wave length detector which in addition to the anthraquinone will given an analysis for sodium sulfate. If only anthraquinone is desired a mercury source ultra violet detector of wave length 254 n.m. is suitable. The detectors of course may be aligned in series so that a single pass through the columns gives the entire story.

In accordance with the present invention an analysis of four of the components of, for example, a Stretford gas treating solution containing sodium vanadate, sodium carbonate, sodium bicarbonate and sodium hydroxide and contaminated with acid gas components and various hydrocarbon gases can be made by diluting an aliquot of the contaminated solution to between about 10 to 1000 times, and, thereafter passing the dilute aliquot through a guard column, conveniently an anion exchange column then through a brine column of the nature hereinafter defined, and into a zinc source ultraviolet detector of the required wave length, e.g. 214 n.m. for vanadium and 190 n.m. for sulfate and anthraquinone. The columns are eluted with a sodium sulfate/sodium hydroxide buffered solution. The entire procedure takes about 20 minutes.

The guard column, conveniently is an anion exchange column found suitable for use in accordance with the aforedescribed procedure is the Dionex, AG.5, medium capacity (0.05 meq./gm) ion exchange resin in bed form treated for analysis of hydrophobic ion, and sulfonated divinyl benzene quarternary ammonium latex form of anion exchange resins.

The only brine column found suitable was Dionex, AS.5-separator of the same general nature treated for brine anaylsis.

The ultra violet detector source metals, such as, Zn which gives a 214 nm wave length is suitable if anyone or more of the four components are to be analyzed for. As noted, other detectors are required to give the anthraquinone and sodium sulfate component analysis.

The process of the present invention requires a standard solution to be made up and run through the two columns. While running one standard is suitable so long as the same columns are being used it is of course sound analytical practice to reconfirm the standard on a regular basis. The analysis can be carried out using glass, plastic or plastic coated columns. The pressure at which the analysis is carried out depends on the nature of the materials of construction of the column, glass of course being the material utilizing the lowest pressure, e.g. about 100 psi, while the plastic and plastic lined metal can be employed up to 1500 psi.

The temperature at which the analysis is run is not critical but preferably should be room temperature, e.g. 20° C. to about 100° C. with 50° C. being a readily acquired, reproducible temperature with instruments suitable for both laboratory and in-plant on-line analysis.

DETAILED DESCRIPTION OF THE INVENTION

A standard solution was prepared to check the accuracy of the designated columns to carry out the chromatographic separations. The standard consisted of:

| g. per liter of | | |
|---|---|---|
| 1.6 | NaOH | combined and referred |
| 0.3 | NaHCO$_3$ | to by the industry |
| 0.3 | Na$_2$CO$_3$ | as total carbonate |
| 0.2 | NaVO$_3$ | alkalinity |
| 0.5 | Na$_2$S$_2$O$_3$.5H$_2$O | |

Twenty microliters of a 0.5 milliliter aliquot of the above solution was processed by injection into an eluant, flowing at 20 ml per min. and consisting of 0.001M Na$_2$SO$_4$ and 0.0004M NaOH. The columns were a 3 mm×150 mm glass ion exchange column "Dionex AG.5" produced by Dionex Corp. and a 3 mm×250 mm glass brine column also produced by Dionex Corp. Each being a medium capacity (0.05 meq./gm) anion exchange resin in bed form treated to analyse for hydrophobic ions. The diluted 0.5 ml aliquot was injected at about 35° C. and about 100 psi. Within 20 minutes, the record of the separations was observed at a detector attenuation of 0.032 AUFS (absorbance units full scale) and a recorder attenuation of 10 millivolts.

The detector was an ultra violet zinc source of 214 n.m.

The accuracy of detection for a composite standard solution was:

| | |
|---|---|
| NaOH | ±1.5% |
| NaHCO$_3$/Na$_2$CO$_3$ | ±4.0% |
| NaVO$_3$ | ±0.95% |
| Na$_2$S$_2$O$_3$ | ±3.0 |

Figure 1:
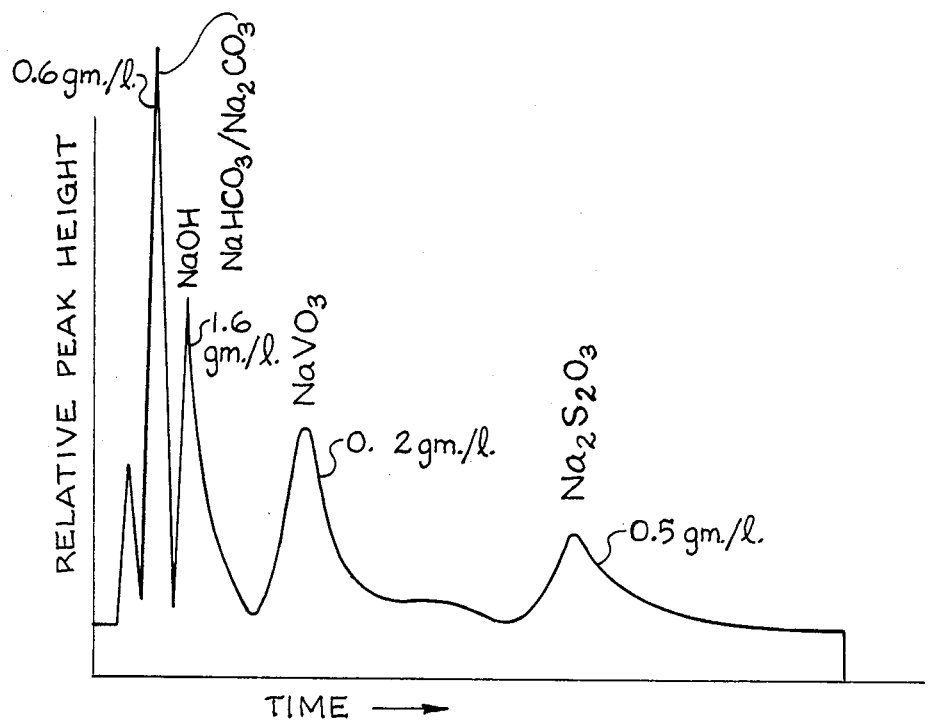
FIGS. 1-4 illustrate results obtained in experiments 1 and 2.

The record obtained with this standard is shown in FIG. 1.

Figure 2:
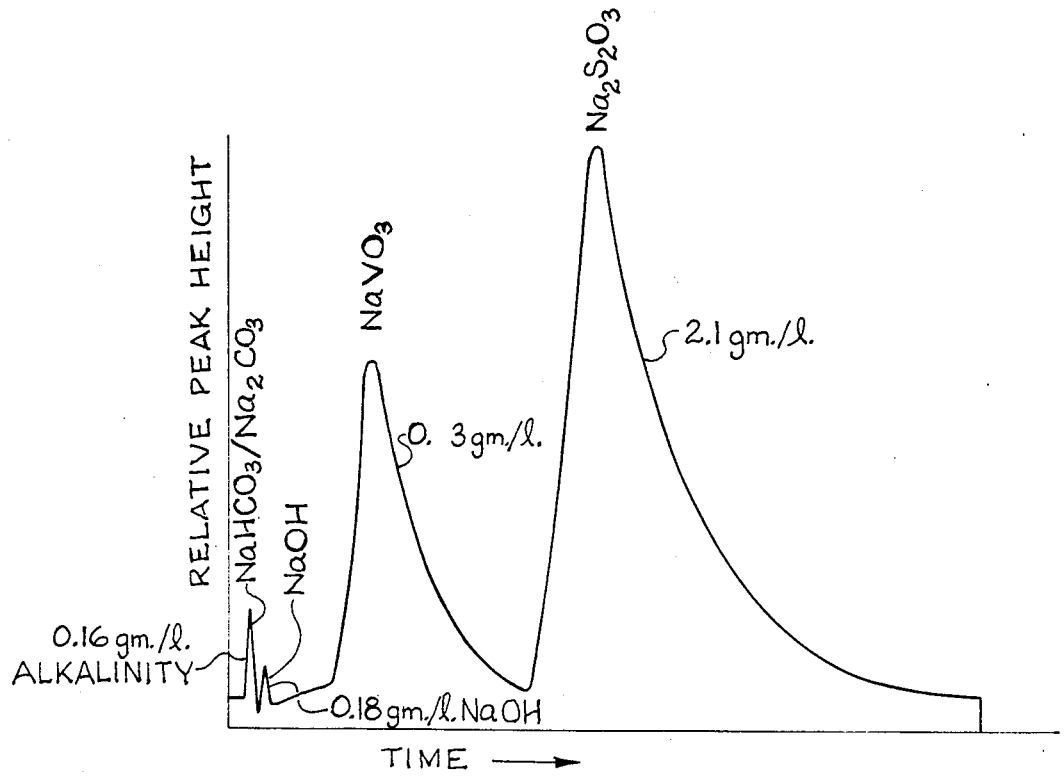

In a similar manner a solution obtained from an operating Stretford process gas treating plant, having a pH of 8.5, was diluted by a factor of 100, 20.0 μl of which was eluted through the same column under the same conditions. The results were obtained in 20 minutes. The recorder chart is shown in FIG. 2. The chart shows the analysis to be 0.16 gm/l total alkalinity (Na$_2$HCO$_3$/NaHCO$_3$); 0.18 gm/l NaOH; 0.03 gm/l V as NaVO$_3$; and, 2.1 gm$^2$/l Na$_2$S$_2$O$_3$.

EXAMPLE 2

Figure 3:
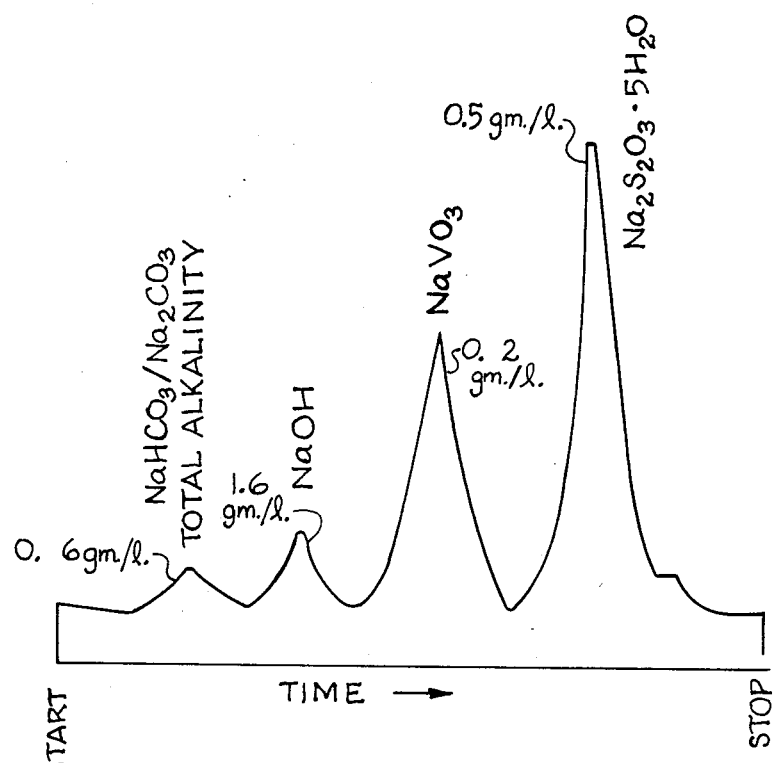
Figure 4:
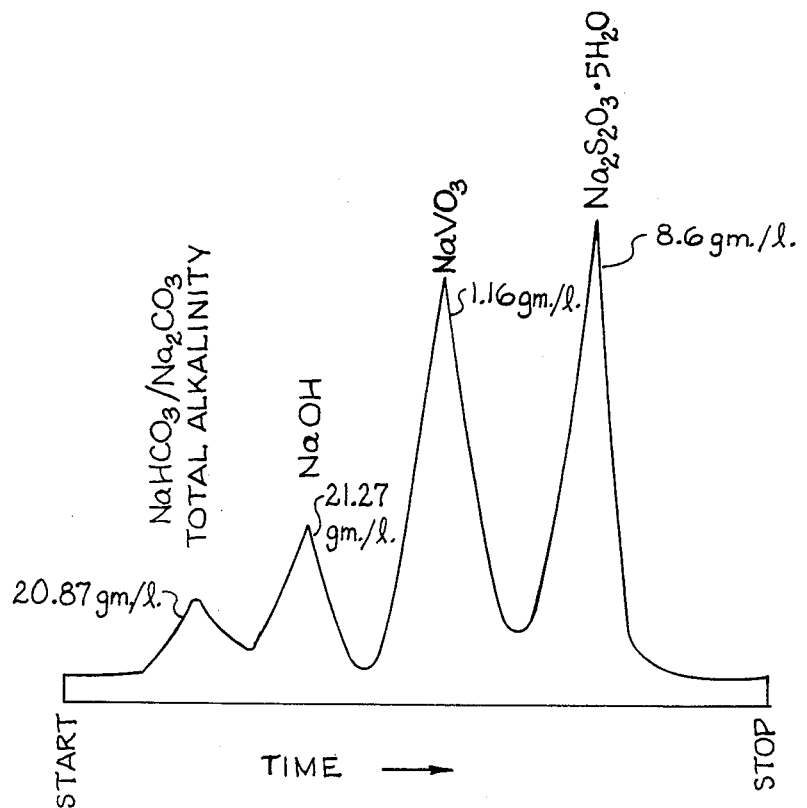

This series of runs employed a reporting integrator (HP 3390) in place of the strip recorder. As in Example 1 a standard was made up and run. The standard was of the same composition as that employed in Example 1. The second sample was from a commercial plant operating the Stretford Process. The results of the recorder record are shown in FIGS. 3 and 4.

The commercial plant analysis taken from the charts shows:

| | Standard gm/l | Commercial solution gm/l |
|---|---|---|
| Total alkalinity (NaHCO$_3$/Na$_2$CO$_3$) | 0.06 | 20.87 |
| NaOH | 1.6 | 21.27 |
| Vanadium | 0.02 | 1.16 |
| Na$_2$S$_2$O$_3$ | 0.5 | 8.6 |

The analysis took 20 minutes when compared to currently available analytical techniques which may be used to analyze the same commercial plant sample, a marked savings in time is achieved by the present technique. Prior to analysis by conventional techniques the solution must be filtered, and twelve chemical solutions prepared and/or standardized to accomodate the various techniques. In addition, the analyses takes about one hour and thirty minutes to complete.

EXAMPLE 3

In this series of runs, the 150 mm×3 mm column in series with the brine column was packed with resin prepared from 17 micron surface sulfonated styrene divinyl benzene copolymer and 6250 angstrom quarternary ammonium latex anion exchanger. The diluted 0.5 ml aliquot sample was injected into the styrene divinyl benzene column, passed through the brine column and into a conductivity detector. The eluent was then passed through an ultraviolet detector at 214 nm. The flow rate was 2.0 ml/min. Peak intensities were recorded with a dualpen strip chart recorder. The sodium sulfate responded to the conductivity detector, and the alkalinity (NaHCO$_3$, Na$_2$CO$_3$), sodium vanadate, and sodium thiosulfate responed to the UV detector (wave length 214 nm). A base line correction was made for the elutant containing 0.001M sodium sulfate on the conductivity detector response peak.

What is claimed is:

1. In a method for determining the presence and amount of sodium vanadate in an aqueous solution containing at least one of the group consisting of sodium hydroxide, sodium acid carbonate, sodium carbonate, sodium thiosulfate, anthraquinone disulfonic acid, various acid gases, hydrocarbon liquid and gases contained in an acid gas treating solution for removing at least one acid gas from natural or synthetic gases containing acid gases, the improvement which comprises:

passing an aliquot of the aqueous solution to be analyzed into and through an anion exchange column selected from the group consisting of medium capacity (0.05 meq./gm) hydrophobic ion exchange column and sulfonated styrene divinyl benzene quaternary ammonium latex anion exchange column; then passing the aliquot through a brine sensitive anion exchange column which has been treated for brine analysis;

eluting the columns with a 0.001M Na$_2$SO$_4$/0.0004M NaOH aqueous eluant solution;

detecting vanadate eluted from the columns in a metal source ultraviolet 214 nanometer detector;

recording a signal from the detector; and comparing the recorded signal to a prerecorded standard of the detected vanadate eluted with the same eluant through the columns thereby obtaining a relative proportion of the detected vanadate with the prerecorded standard.

2. In a method for determining the presence and amount of sodium hydroxide, sodium acid carbonate, sodium carbonate, sodium vanadate and sodium thiosulfate in an aqueous solution containing at least one of the group consisting of anthraquinone disulfonic acid, various acid gases, hydrocarbon liquid and gases contained in an acid gas treating solution for removing at least one acid gas from natural or synthetic gases containing acid gases, the improvement which comprises:

passing an aliquot of the solution to be analyzed into and through a hydrophobic anion exchange column; then passing the aliquot through a brine sensitive anion exchange column which has been treated for brine analysis;

eluting the columns with a 0.001M $Na_2SO_4$/0.0004M NaOH aqeous eluant solution;

detecting sodium vanadate eluted in a metal source ultraviolet 214 nanometer detector and the presence of sodium carbonate, sodium bicarbonate, sodium hydroxide and sodium thiosulfate eluted in a zinc source ultraviolet detector;

recording signals from each detector; and comparing the recorded signals of the detected compounds to prerecorded standards of the detected compounds eluted with the same eluant through the columns thereby obtaining relative proportions of the detected compounds with the prerecorded standards.

3. In a method for determining the presence and amount of anthraquinone disulfonic acid, sodium hydroxide, sodium acid carbonate, sodium carbonate, sodium vanadate and sodium thiosulfate in an aqueous solution containing at least one of the group consisting of various acid gases, hydrocarbon liquid and gases contained in an acid gas treating solution for removing at least one acid gas from natural or synthetic gases containing acid gases, the improvement which comprises:

passing an aliquot of the aqueous solution to be analyzed into and through an anion exchange column; then passing the aliquot through a brine sensitive anion exchange column, each column being a medium capacity (0.05 meq./gm.) hydrophobic anion exchange column;

eluting the columns with a 0.001M $Na_2SO_4$/0.0004M NaOH aqeous eluant solution;

detecting anthraquinone and sodium sulfate in an ultraviolet 190 or 254 nanometer detector and the presence of a remainder of alkalinity components eluted from the columns in a serially connected conductivity cell;

recording signals from each detector; and comparing the recorded signals of the detected compounds to prerecorded standards of the detected compounds eluted with the same eluant through the columns thereby obtaining relative proportions of the detected compounds with the prerecorded standards.

4. In a method for determining the presence and amount of sodium hydroxide, sodium acid carbonate, sodium carbonate, sodium vanadate, sodium thiosulfate and anthraquinone in an aqueous solution containing sodium hydroxide, sodium acid carbonate, sodium carbonate, sodium vanadate, sodium thiosulfate and anthraquinone and at least one selected from the group consisting of various acid gases, hydrocarbon liquid and gases contained in an acid gas treating solution for removing at least one acid gas from natural or synthetic gases containing acid gases, the improvement which comprises:

passing an aliquot of the aqueous solution to be analyzed into and through an anion exchange column; then passing the aliquot through a brine sensitive anion exchange column, each column being a medium capacity (0.05 meq./gm.) hydrophobic anion exchange column;

eluting the columns with a 0.001M $Na_2SO_4$/0.004M NaOH aqueous eluant solution;

detecting sodium hydroxide, sodium carbonate, sodium bicarbonate and sodium thiosulfate eluted from the columns in a zinc source ultraviolet detector and vanadate and sodium sulfate eluted from the columns in a deuterium and mercury source ultraviolet detector;

recording signals from each detector; and comparing the recorded signals of the detected to prerecorded standards of the detected compounds eluted with the same eluant through the columns thereby obtaining relative proportions of the detected compounds with the prerecorded standards.

* * * * *

UNITED STATES PATENT AND TRADEMARK OFFICE
CERTIFICATE OF CORRECTION

PATENT NO. : 4,749,656
DATED : June 7, 1988
INVENTOR(S) : LaVerne W. Ellerbe

It is certified that error appears in the above-identified patent and that said Letters Patent is hereby corrected as shown below:

FIGURE 1, "0. 2gm./l." should read --0.02gm./l.--.

FIGURE 2, "0. 3gm./l." should read --0.03gm./l.--.

FIGURE 3, "0. 6gm./l." should read --0.06gm./l.--, and "0. 2gm./l." should read --0.02gm./l.--.

Column 1, line 53, "Similarily" should read --Similarly--.

Column 2, line 13, "given" should read --give--.

Column 2, line 44, "anaylsis" should read --analysis--.

Column 3, line 44, "$\pm 3.0$" should read --$\pm 3.0\%$--.

Column 4, line 35, "responed" should read --responded--, and line 37, "elutant" should read --eluant--.

Column 5, line 18, "aqeous" should read --aqueous--.

Column 6, line 2, "aqeous" should read --aqueous--.

Signed and Sealed this

Fifteenth Day of August, 1989

Attest:

DONALD J. QUIGG

Attesting Officer

Commissioner of Patents and Trademarks